United States Patent [19]

Imamura et al.

[11] Patent Number: 5,783,209
[45] Date of Patent: Jul. 21, 1998

[54] MEDICAL PRESSURE-SENSITIVE ADHESIVE AND MEDICAL DRESSING MATERIAL PROVIDED WITH THE SAME

[75] Inventors: Kengo Imamura; Hirofumi Sonoda; Yorinobu Takamatsu; Hiroyasu Nanakubo, all of Sagamibara, Japan

[73] Assignee: Minnesota Mining and Manufacturing Company, St. Paul, Minn.

[21] Appl. No.: 801,232

[22] Filed: Feb. 19, 1997

Related U.S. Application Data

[63] Continuation of Ser. No. 414,578, Mar. 31, 1995, abandoned.

[30] Foreign Application Priority Data

Apr. 1, 1994 [JP] Japan ................... 6-064890

[51] Int. Cl.$^6$ ................... A61F 13/02
[52] U.S. Cl. ................... 424/448; 424/449; 428/355
[58] Field of Search ................... 424/448, 449; 428/355

[56] References Cited

U.S. PATENT DOCUMENTS

| 3,441,430 | 4/1969 | Peterson | 428/354 |
|---|---|---|---|
| 4,077,926 | 3/1978 | Sanderson et al. | 524/558 |
| 4,693,776 | 9/1987 | Krampe | 156/237 |
| 4,714,655 | 12/1987 | Bordoloi | 428/345 |
| 4,759,983 | 7/1988 | Knutson | 428/343 |
| 4,879,178 | 11/1989 | Sun | 428/355 |
| 4,908,403 | 3/1990 | Spada | 525/818 |
| 5,175,052 | 12/1992 | Tokuda et al. | 428/355 |
| 5,429,590 | 7/1995 | Saito et al. | 602/48 |

FOREIGN PATENT DOCUMENTS

| 0 369 092 | 5/1990 | European Pat. Off. |  |
|---|---|---|---|
| 0 427 877 | 5/1991 | European Pat. Off. |  |
| 0 369 092 | 12/1993 | European Pat. Off. | A61L 15/58 |
| 0 601 463 | 6/1994 | European Pat. Off. |  |
| S54-6276 | 3/1979 | Japan . |  |
| H1-47509 | 10/1989 | Japan . |  |
| S55-14108 | 4/1990 | Japan . |  |
| 2-232048 | 9/1990 | Japan | A61F 13/02 |
| 4-150865 | 5/1992 | Japan | A61L 15/58 |
| 4-272754 | 9/1992 | Japan | A61F 13/00 |
| 4-272764 | 9/1992 | Japan | A61L 15/16 |
| H7-118144 | 5/1995 | Japan . |  |
| 84/03837 | 10/1984 | WIPO | A61L 15/06 |
| 91 14461 | 10/1991 | WIPO . |  |

OTHER PUBLICATIONS

Database WPI, Derwent Publications Ltd., Abstract of JP A 04 150 865 (May, 1992).

Database WPI, Derwent Publications Ltd., Abstract of JP A 04 272 754 (Sep. 1992).

Database WPI, Derwent Publications Ltd., Abstract of JP A 04 272 764 (Sep. 1992).

*Primary Examiner*—D. Gabrielle Brouillette
*Attorney, Agent, or Firm*—Robert W. Sprague; Myra H. McCormack; Stephen W. Bauer

[57] ABSTRACT

A medical pressure-sensitive adhesive is provided, having a high steam permeability (at least 1100 g/(m$^2$·24 Hr) at a temperature of 37° C. and an RH of 40%), and exhibiting such an appropriate adhesive strength as the dressing material coated with the pressure-sensitive adhesive is not easily peeled off and a wound is not inflicted on the skin when the dressing material is peeled from the skin, and also exhibiting durability of such an appropriate adhesive strength as well as an appropriate cohesive force. A medical pressure-sensitive adhesive, comprising a polymer containing above 50 wt % of a unit derived from an alkoxyalkyl acrylate, the Tg value of the homopolymer thereof being −35° C. or less is also provided.

7 Claims, No Drawings

MEDICAL PRESSURE-SENSITIVE ADHESIVE AND MEDICAL DRESSING MATERIAL PROVIDED WITH THE SAME

This is a continuation of application Ser. No. 08/414,578 filed Mar. 31, 1995 now abandoned.

TECHNICAL FIELD

The present invention relates to a medical pressure-sensitive adhesive used for medical dressing material and the like, which is an article for the use of the medical treatment of the wound of a human body or the like.

BACKGROUND ART

Japanese Unexamined Patent Publication (Kokai) No. 2-232048 proposes, for the purpose of providing an externally applicable sticker capable of preventing the skin from being poisoned therewith and having both sufficient adhesiveness to the skin and cohesive force as an adhesive, an externally applicable sticker with a pressure-sensitive adhesive on one side of a base film, said adhesive being a copolymer composed of 40 of 80 wt % of a monomer of an alkylester of methacrylic acid, 10 to 50 wt % of an alkoxy group-containing ethylenic unsaturated monomer, and 1 to 10 wt % of a carboxyl group-containing ethylenic unsaturated monomer, the Tg value of the copolymer being 250° K. or less, and the gel fraction of the copolymer after drying being 25 wt % or more. The alkoxy group-containing ethylenic unsaturated monomer used for the formation of the aforesaid adhesive contains an alkoxyalkyl acrylate. It is mentioned in this publication that the reason why the content of this alkoxy group-containing ethylenic unsaturated monomer in the aforesaid copolymer is set to a value of 50 wt % or less is that when this content exceeds 50 wt %, the hydrophilicity of the polymer becomes too high, and the adhesiveness of the adhesive to the skin becomes lowered. This adhesive is low in steam permeability. For example, the highest steam permeability shown in the working examples is 100 g/(m²·24 hours) at a temperature of 40° C. and an RH of 30%.

Japanese Unexamined Patent Publication (Kokai) No. 4-150865 proposes, for the purpose of providing a medical pressure-sensitive adhesive tape excellent in adhesiveness to the skin and low in skin irritation, a pressure-sensitive adhesive tape with a crosslinked type pressure-sensitive adhesive layer provided on a flexible backing, in which the aforesaid crosslinked type pressure-sensitive adhesive layer contains a crosslinked material of a copolymer consisting of 99 to 99.9 wt % of a mixture of an alkyl acrylate and an alkoxyalkyl acrylate, the alkoxyalkyl acrylate content being 50 wt % or less, and 0.1 to 1 wt % of a carboxyl group and/or hydroxyl group-containing monomer. It is mentioned in this publication that the reason why the amount of the alkoxyalkyl acrylate used in this copolymer is set to a value less than 50 wt % is for the purpose of preparing a pressure-sensitive adhesive having well-balanced combined properties such as adhesiveness to the skin, medicine solubility, and medicine stability. However, this pressure-sensitive adhesive is low in steam permeability, like that of the aforesaid Japanese Unexamined Patent Publication No. 2-232048.

Japanese Unexamined Patent Publication (Kokai) No. 4-272754 proposes, for the purpose of providing an adhesive dressing having adhesiveness, air permeability, and antimicrobial activity, an adhesive dressing, comprising an adhesive layer laminated on one side of a film of thermoplastic polyurethane elastomer, and a hydrophilic porous film laminated on a part of the surface of said adhesive layer. This hydrophilic porous film is prepared by grafting an alkoxyalkyl acrylate such as methoxyethyl acrylate and/or alkylacrylamide onto a film of porous polyolefin or the like. As an example of the aforesaid alkoxyalkyl acrylate, there is mentioned methoxyethyl acrylate or methoxyethyl methacrylate. However, the polymer formed by grafting methoxyethyl acrylate or the like is used for the purpose of imparting hydrophilicity to the porous film, but has no function as a pressure-sensitive adhesive.

Japanese Unexamined Patent Publication (Kokai) No. 4-272764 proposes, for the purpose of providing a wound-covering material exhibiting excellent adhesive strength to the wounded surface of the skin, not being easily decomposed and released when contacted with the wounded region, having both steam permeability and liquid permeability, and capable of maintaining suitable humidity at the wounded surface of the skin, thereby contributing to the cure of the wounded region, a wound-covering material, comprising a hydrophilic polymer layer formed by a chemical bonding on the surface of a film of thermoplastic polyurethane elastomer. As an example of the aforesaid hydrophilic polymer, there is mentioned formation of a hydrophilic polymer by grafting of a homopolymer or copolymer of an alkoxyalkyl acrylate. However, this grafted polymer is used for the purpose of imparting hydrophilicity to the film, but has no function as a pressure-sensitive adhesive, like in the aforesaid example.

SUMMARY OF THE INVENTION

The present invention provides a pressure-sensitive adhesive for medical care, which exhibits high steam permeability [at least 1100 g/(m²·24 hours) at a temperature of 37° C. and an RH of 40%], appropriate adhesive strength in such a degree as the dressing material is not easily peeled off and does not inflict a wound on the skin when it is peeled off, and also exhibits durability of such suitable adhesion as well as a suitable cohesive force.

DETAILED DESCRIPTION OF THE INVENTION

The first aspect of the present invention is a pressure-sensitive adhesive for medical care, comprising a polymer containing a unit derived from an alkoxyalkyl acrylate, the Tg value of the homopolymer of which is −35° C. or less, in a proportional amount exceeding 50 wt %. The unit is one which is derived from vinyl polymerization of acrylate.

The pressure-sensitive adhesive of the present invention achieves a high steam permeability by introduction of a highly hydrophilic alkoxyl group into the alkyl group portion of an alkyl acrylate. In addition, since such an alkoxyalkyl acrylate is water insoluble, it is not liable to be influenced by the moisture caused by perspiration and the like, and gives a polymer maintaining, even after elapse of time, a cohesive force and a suitable adhesive force in such a degree as the dressing material is not easily peeled from the skin and does not inflict a wound on the skin when the dressing material is forced to be peeled off.

The alkoxyalkyl acrylate from which the pressure-sensitive adhesive of the present invention is originated has a Tg value of the homopolymer thereof being −35° C. or less, preferably −40° C. or less, and more preferably, −50° C. or less. Though the lower limit of the Tg value is not particularly set, it is preferably about −80° C. The reason thereof is that alkoxyalkyl acrylates having a Tg value of the homopolymer thereof being lower than −80° C. are not easily available, and that there is a fear that such compounds would lower the cohesive force of the pressure-sensitive adhesive of the present invention. The Tg value herein referred to is the peak temperature of tan 6 when measured in a compression mode and at a measurement frequency of 1 radian/sec by use of a dynamic viscoelasticity measuring device ["RSA-II" (trade mark) produced by Rheometrix Inc.]. The reason why the Tg value is herein set to a value of −35° C. or less is for the purpose of obtaining an appropriate adhesive strength, and when the Tg value is −40° C. or less, and further, −50° C. or less, more suitable adhesive strength can be obtained.

As the aforesaid alkoxyalkyl acrylate having a Tg value of the homopolymer thereof being −35° C. or less, those having an alkoxyalkyl group containing 4 to 8 carbon atoms are preferable, in view of the easiness of the control of the Tg value, and those having an alkoxyalkyl group containing 6 to 8 carbon atoms are more preferable. With respect to the alkoxyalkyl group, there may be exemplified straight-chain groups such as methoxypropyl, ethoxyethyl, methoxybutyl, ethoxypropyl, propoxyethyl, methoxypentyl, ethoxybutyl, propoxypropyl, butoxyethyl, methoxyhexyl, ethoxypentyl, propoxybutyl, butoxypropyl, pentoxyethyl, methoxyhepthyl, ethoxyhexyl, propoxypentyl, butoxybutyl, pentoxypropyl, hexyloxyethyl groups etc., and branched groups such as 2-methoxybutyl, 3-methoxybutyl groups, etc.

The reason why the amount of the unit derived from an alkoxyalkyl acrylate is set to a value exceeding 50 wt % is for the purpose of obtaining a high steam permeability, for example, a steam permeability of 1100 g/($M^2$·24 hours) or more at a temperature of 37° C. and an RH of 40%. This amount is preferably within the range between 55 and 97 wt %, more preferably between 60 and 95 wt %. When this amount is within the range between 55 and 97 wt %, there is obtained more excellent steam permeability and a suitable cohesive force. A suitable cohesive force does not cause cohesive failure when it is applied to the skin and the like and thereafter peeled off, and has a hereafter-mentioned LIFT less than 10%, and when the amount is within the range between 60 and 95 wt %, the steam permeability is further improved, and the scattering of adhesion becomes smaller.

The second aspect of the present invention is a pressure-sensitive adhesive for medical dressing material, containing a unit derived from an alkoxyalkyl acrylate having a Tg value of the homopolymer thereof being −35° C. or less (hereinafter referred to as "component 'a'") in a proportional amount exceeding 50 wt %, and a unit derived from a vinyl monomer having a Tg value of the homopolymer of itself being 25° C. or more (hereinafter referred to as "component 'b'") in a proportional amount ranging from 0.1 to 20 wt %. Any of the above unit is one which is derived from vinyl polymerization of the vinyl group inherent in the monomer.

With respect to component "a," what has been mentioned in the first aspect of the present invention exactly fits. The reason of existence of component "b" resides in obtaining a higher cohesive force without impairing other properties by itself. That is, the reason why the Tg value of component "b" is required to be 25° C. or more is that when Tg is less than 25° C., it is difficult to obtain a high cohesive force. In addition, when the Tg value is 35° C. or more, and more preferably, 50° C. or more, there is obtained a further higher cohesive force with a small amount of this component without degrading other properties.

The amount of the component "b" is within the range between 0.1 and 20 wt %. When this amount is less than 0.1 wt %, it is difficult to obtain a higher cohesive force as compared with the case of component "a" alone. When this amount exceeds 20 wt %, the wettability becomes lowered and suitable adhesiveness cannot be obtained. The amount of the component "b" is, more preferably, within the range between 0.5 and 18 wt %. Within this range of component "b," the cohesive force and adhesive strength of the adhesive as a medical pressure-sensitive adhesive are well balanced, and during its application to the skin, the pressure-sensitive adhesive sufficiently adheres to the skin. When the dressing material is peeled off, there is no fear that the pressure-sensitive adhesive remains on the skin. In addition, the amount of the component "b" is, further more preferably, within the range between 1 and 15 wt %. Within this range of component "b," the cohesive force and adhesion become better balanced.

Examples of component "b" include but are not limited to units derived from a polar monomer, units derived from acrylic acid, methacrylic acid, acrylamide, methacrylamide, dialkylacrylamides and dialkylmethacrylamides such as N,N-dimethylacrylamide and N,N-dimethylmethacrylamide, N-vinyl-2-pyrrolidone, vinyl pyrrolidone, and the like, and as units derived from a non-polar monomer, the units derived from polystyrene macromonomers. These are used alone or in combination of 2 or more of them.

The third aspect of the present invention is a medical pressure-sensitive adhesive, containing component "a" mentioned in the second aspect of the present invention in a proportional amount exceeding 50 wt %, component "b" mentioned also in the second aspect in a proportional amount ranging from 0.1 to 20 wt %, a unit derived from a vinyl monomer having a Tg value of the homopolymer thereof (hereinafter referred to as "component 'c'") being less than 25° C., except for component "a," in a proportional amount ranging from 0.1 to 49.9 wt %.

Component "c" exists for the purpose of further improving the balance between adhesiveness and cohesive force of the pressure-sensitive adhesive of the present invention, or for the purpose of further improving the steam permeability of the present pressure-sensitive adhesive.

The amount of the component "c" is within the range between 0.1 and 49.9 wt %. When the amount of component "c" is less than 0.1 wt %, the existence of component "c" is less effective, and on the other hand, when this amount exceeds 49.9 wt %, the steam permeability of the pressure-sensitive adhesive becomes lowered, or the cohesive force of the present adhesive becomes lowered. The more preferable range of the amount of component "c" is between 0.5 and 40 wt %. Within this range of the amount of component "c," the functions of component "c" (improvement of the balance between the adhesiveness and cohesive force of the pressure-sensitive adhesive of the present invention and improvement of the steam permeability of the present pressure-sensitive adhesive) become higher, and when this amount is within the range between 1 and 30 wt %, these functions became even higher.

As examples of component "c," there may be mentioned alkyl acrylates and alkyl methacrylates having an alkyl group containing 4 to 12 carbon atoms, e.g., butyl acrylate, butyl methacrylate, hexyl acrylate, hexyl methacrylate, isooctyl acrylate, isooctyl methacrylate, n-octyl acrylate, n-octyl methacrylate, 2-ethylhexyl acrylate, 2-ethylhexyl methacrylate, isononyl acrylate, isononyl methacrylate, dodecyl acrylate, dodecyl methacrylate and the like; alkoxyalkyl acrylates and alkoxyalkyl methacrylates having an alkoxyalkyl group containing 3 carbon atoms, e.g., methoxyethyl acrylate and methoxyethyl methacrylate; hydroxyalkyl acrylates and hydroxyalkyl methacrylates having a hydroxyalkyl group containing 2 to 10 carbon atoms, e.g., hydroxyethyl acrylate, hydroxyethyl methacrylate, hydroxypropyl acrylate, hydroxypropyl methacrylate, hydroxybutyl acrylate, hydroxybutyl methacrylate, and the like; and alkoxypoly(alkylene glycol) acrylates and alkoxypoly (alkylene glycol) methacrylate, e.g., methoxypoly(ethylene glycol) acrylate and methoxypoly(ethylene glycol) methacrylate having 9 or 16 repeating units of ethylene glycol, and methoxypoly(tetramethylene glycol) acrylate having 222 repeating units of tetramethylene glycol.

When the number of carbon atoms contained in the alkyl group of the aforesaid alkyl acrylates and alkyl methacrylates is 3 or less, the Tg value becomes high, and there is a fear that the adhesion of the pressure-sensitive adhesive should become lowered. On the other hand, when the number of carbon atoms is 13 or more, there is a fear that the steam permeability of the pressure-sensitive adhesive should become lowered.

With respect to the aforesaid alkoxyalkyl acrylates and alkoxyalkyl methacrylates containing 3 carbon atoms, when any of them is present in a predetermined amount, it improves the steam permeability of the pressure-sensitive adhesive, while the adhesive strength of the present adhesive is prevented from becoming lowered. Such kinds of compounds having an alkoxyalkyl group containing 2 carbon atoms are not easily available.

Of the aforesaid hydroxy acrylates and hydroxy methacrylates, those having a hydroxyalkyl group containing 1 or 11 or more carbon atoms are not easily available.

The number of carbon atoms contained in the alkylene glycol of the aforesaid alkoxypoly(alkylene glycol) acrylates and alkoxypoly(alkylene glycol) methacrylates is preferably within the range between 2 and 4. In addition, the number of the repeating units of alkylene glycol is preferably within the range between 2 and 300. When the number of carbon atoms and number of repeating units are without these ranges, respectively, there is a fear that the steam permeability of the pressure-sensitive adhesive should become lowered.

In addition, by adding crosslinking agent to the pressure-sensitive adhesive of the present invention, a cohesive force can be heightened to the pressure-sensitive adhesive. For example, a crosslinking agent such as isocyanate, epoxy, aziridine, phenol type crosslinking agents, etc., may be added for the purpose of improving the cohesive force of the pressure-sensitive adhesive. A crosslinking agent is added preferably in a proportional amount ranging from 0.01 to 1 wt %. When the amount of the crosslinking agent is less than 0.01 wt %, the pressure-sensitive adhesive becomes poor in crosslinkability and when the amount exceeds 1 wt %, the pressure-sensitive adhesive becomes poor in tackiness.

In addition, medicinals may be added to the pressure-sensitive adhesive of the present invention. Examples of medicines suitable to add to the adhesives include, antibacterial substances, hypnotic and sedative drugs, antipyretic, analgetic and resolutive drugs, stimulant and antihypnotic drugs, dizziness-alleviating drugs, drugs for psychoneurosis, skeletal muscle-relaxing drugs, anticonvulsants, antiparkinsonisms, antihistamines, cardiacs, drugs for arrhythmia, hypotensive drugs, angiotonics drugs, coronary blood vessel dilators, peripheral blood vessel dilators, other drugs for circulatory organs, respiration promoters, antitussive and expectorant drugs, various hormones, medicines for external application for suppurative diseases, pain-killing antipruritic stegnotic antiphlogistic drugs, drugs for parasitic cutaneous diseases, various vitamins, hemostatic agents, blood coagulation inhibitors, antidotes, drugs for habitual intoxication, drugs for diabetics, malignant tumor-resisting drugs, and drugs exhibiting pharmacological actions such as anesthesia. The amount of any of these medicinals is preferably within the range between 0.05 and 25 wt % in order that suitable adhesive strength, cohesive force and effect of medicine may be obtained.

In addition, a plasticizer may be added to the pressure-sensitive adhesive of the present invention to obtain appropriate adhesive strength, cohesive force and plasticizing effect. Examples of this plasticizer include mentioned polyols, such as polyethylene glycol, polypropylene glycol, glycerine and the like. Any of these plasticizers is to be added preferably in a proportional amount ranging from 0.1 to 10 wt %.

Furthermore, by addition of hydrophilic polymer particles to the pressure-sensitive adhesive of the present invention, the water absorbing power of the pressure-sensitive adhesive can be increased. The examples of these hydrophilic polymer particles hydrogel are partially crosslinked materials such as polyvinyl alcohol, polyacrylamide, polyvinyl pyrrolidone, and the like. Any of these hydrophilic polymer particles is to be added preferably in a proportional amount ranging from 0.1 to 30 wt %, in consideration of suitable adhesive strength, cohesive force and water absorption effect of the pressure-sensitive adhesive of the present invention.

In addition, a tackifier can be added to the pressure-sensitive adhesive of the present invention in order to improve the adhesive strength and tackiness of the pressure-sensitive adhesive. Examples of this tackifier include but are not limited to rosin-type, terpene-type, petroleum resin-type tackifiers, and the like. Any of these tackifiers is to be added preferably in a proportional amount ranging from 1 to 30 wt %, in consideration of the suitable adhesive strength and cohesive force of the pressure-sensitive adhesive of the present invention.

In addition, a filler can be added to the pressure-sensitive adhesive of the present invention. It is thereby possible to increase the cohesive force of the pressure-sensitive adhesive of the present invention, reduce the cost thereof, and further impart oxidation-preventing effect thereto. Examples of this filler include talc, calcium carbonate, clay, kaolin, silica, barium sulfate, kaolin sulfate, aluminium hydroxide, zinc oxide, calcium oxide, titanium oxide, alumina, mica, bentonite, and the like.

The pressure-sensitive adhesive of the present invention can be made by polymerizing a monomer, from which the unit of the polymer in any of the aforesaid first to third embodiments is derived, by the following methods. For example, there may be adopted solution polymerization, emulsion polymerization, bulk polymerization, suspension polymerization and the like. In particular, emulsion polymerization and suspension polymerization are preferable because the molecular weight of the polymer becomes high and the cohesive force thereof becomes high; solution polymerization is preferable because the molecular weight distribution is comparatively narrow and the irregularity of adhesive strength is slight; and bulk polymerization is favorable because no solvent is used.

The pressure-sensitive adhesive of the present invention is preferably irradiated in order to impart crosslinking, also for the purpose of being sterilized, after or before it is laminated on the backing so as to be formed into a medical dressing material. As the radiation, there may be used γ-rays such as cobalt 60, electron beams, and the like. The irradiation dose is preferably within the range between 1 and 100 kGy. In addition, in the hereafter-mentioned Examples 2 and 8, γ-rays of cobalt 60 were irradiated by a radiation-irradiating device such that the irradiated dose became 10 kGy. As a result, the pressure-sensitive adhesives in Examples 2 and 8 were partially crosslinked, and when the gel content proportions were determined by use of a Soxhlet extractory, they were found to be 42% in Example 2 and 60% in Example 8.

By coating the pressure-sensitive adhesive onto a backing by a knife coater, roll coater, dye coater or the like, it is possible to prepare a dressing material. In addition, it is also possible to apply the pressure-sensitive adhesive to a released paper and subsequently laminate it on a backing by a laminator, such that the pressure-sensitive adhesive may be in contact with the backing. After completion of the aforesaid application of the pressure-sensitive adhesive, the pressure-sensitive adhesive is preferably dried for a period of time ranging from 1 to 10 minutes at an oven temperature ranging from 50° to 120° C.

The thickness of the pressure-sensitive adhesive thus coated on the backing is preferably within the range between 10 and 100 μm. When the thickness is less than 10 μm, the adhesive force of the dressing material becomes low, and on the other hand, when the thickness exceeds 100 μm, coating and drying of the pressure-sensitive adhesive become difficult.

The adhesive strength of the thus prepared dressing material to the skin is preferably within the range between 30 and 500 g/inch. When the adhesive strength is less than 30 g/inch, the dressing material is easily peelable, and when the adhesive strength exceeds 500 g/inch, there is a fear that wound should be inflicted on the skin. This adhesive strength is, more preferably, within the range between 40 and 400 g/inch, and most preferably between 50 and 300 g/inch.

As the material of this backing, there may favorably used the materials excellent in steam permeability or formable into a steam permeable structure, e.g., polyether urethane, polyester urethane, polyether-polyamide block copolymer, polyacrylate, polymethacrylate, polyethylene, polypropylene, polyamide, polyester, fluorine type resins and the like.

Polyether urethane is favorable because it is appropriately stretchable and particularly excellent in steam permeability. Polyester urethane is also favorable because it is suitably stretchable and more inexpensive than polyether urethane, and polyether-polyamide copolymer is also preferable because it is appropriately stretchable and excellent in steam permeability. Polyacrylate and polymethacrylate are preferable because these are high in steam permeability and excellent in weather resistance. Polyethylene, polypropylene and polyester are also preferable because these are easily fabricable, they are appropriately stretchable even at a low temperature, and can be formed into structures excellent in steam permeability.

The aforesaid backing may be in the forms such as woven cloth, non-woven cloth, porous film, and film molded product. Woven cloth, non-woven cloth and porous film are favorable because these are excellent in steam permeability, and film molded product is preferable because it is excellent in bacteria shieldability and water-proofness.

The thickness of the aforesaid backing is favorably within the range between 10 and 100 μm. When the thickness is less than 10 μm, the backing creases very easily and its use operation is difficult, and, on the other hand, when the thickness exceeds 100 μm, the backing becomes difficult to follow up the motion of the skin. The thickness of the backing is preferably within the range between 15 and 60 μm, and more preferably between 20 and 40 μm.

This backing may be transparent, semitransparent or opaque. A transparent backing is most preferable, because the applied portion is visual therethrough. This backing may preliminarily be treated with a primer. In this case, the adhesive force between the backing and the pressure-sensitive adhesive is increased, and this case is therefore preferable. This backing may preliminarily be subjected to back treatment. That is, it is favorable to treat the back of the backing with silicone or a fluorine type resin, for the purpose of release treatment.

In the following, the present invention will be explained with reference to working examples, but it is to be noted that the present invention is not limited to these working examples. In the following working examples and comparative examples, all "parts" are to be construed as "parts by weight," otherwise specified.

EXAMPLES 1 TO 23, COMPARATIVE EXAMPLE 1 TO 6

300 parts of ethyl acetate as a polymerization solvent, 0.3 part of azobisisobutylonitrile as an initiator, and the monomers set forth in the following Tables 1 to 2, respectively, in the amounts set forth in Tables 1 and 2, were introduced in a reactor, and the interior of the reactor was replaced by nitrogen, whereafter polymerization was carried out for 20 hours at a temperature of 55° C. The thus obtained polymers were subjected to the following tests.

Measurement of Steam Permeability

The aforesaid polymers were, respectively, coated as a pressure-sensitive adhesive, onto a silicone-treated release paper with a thickness of 50 μm, such that the weight of the coated pressure-sensitive adhesive after drying became 25 gm$^2$ and the thickness thereof became 25 μm, and subsequently, dried for 10 minutes at a temperature of 65° C. Subsequently, the aforesaid pressure-sensitive adhesive was laminated on a porous polyethylene film with a thickness of 80 μm as a backing, such that the pressure-sensitive adhesive was in contact with the backing, whereafter the aforesaid release paper was peeled off so as to be used as a measurement sample. The aforesaid porous polyethylene film had a steam permeability of 12,000 g/m$^2$ measured by the hereinmentioned method, this value being far higher as compared with the steam permeability of the pressure-sensitive adhesive. 20 g of distilled water were introduced into an aluminium vessel, and the top of the vessel was sealed, with the pressure-sensitive adhesive layer of the above sample placed down, so that the distilled water was not in contact with the aforesaid pressure-sensitive adhesive. This vessel was introduced into a constant temperature and constant humidity tank, and the amount of water reduced from the vessel was determined, whereupon the steam permeability of the pressure-sensitive adhesive layer was calculated. The results are set forth in Tables 1 and 2.

Measurement of Adhesive Strength

The aforesaid polymer was coated as a pressure-sensitive adhesive on a silicone release paper with a thickness of 50 μm, such that the weight of the coated pressure-sensitive adhesive became 25 g/m$^2$ after drying, and the thickness thereof became 25 μm, and dried for 10 minutes at a temperature of 65° C. Subsequently, a highly steam permeable polyether urethane film with a thickness of 30 μm in Examples 1 to 9 and Comparative Examples 1 to 6, a highly steam permeable polyether polyamide film with a thickness of 40 μm in Examples 10 to 16, and a highly steam permeable porous polyethylene film with a thickness of 40 μm in Examples 17 to 23, as a backing, were, respectively, laminated with the coated pressure-sensitive adhesive, so that test pieces of 2.54 cm (1 inch)×7.56 cm (3 inches) were prepared as samples for the measurement of adhesive strength. In order to determine the adhesive strengths to the skin, 1800 peel strengths (g/2.54 cm (1 inch)) were determined by use of the skin of the healthy normal persons. As the testing rate, there was adopted 15.2 cm (6 inches)/min. Each of the aforesaid test pieces was pasted onto the skin of a healthy normal person, and the adhesive strength (g/2.54 cm (1 inch)) measured immediately thereafter was named T0. In addition, the adhesive strength (g/2.54 cm (1 inch)) measured 48 hours after the test piece had been pasted onto the skin of the healthy normal person was named T48, and the average area of the sample peeled off from the skin at that time was named LIFT. The results are set forth in Tables 1 and 2.

TABLE 1

| Examples | Composition/ Compounded Parts | Irradiation of γ-Rays | Tg (°C.) | Water Permeability (g/m · 24-hr.) | T0 (g/inch) | T48 (g/inch) | Failure Mode | LIFT (%) |
|---|---|---|---|---|---|---|---|---|
| 1 | BOEA/ACM 95/5 | no | −36 | 2296 | 172 | 320 | interface | <10 |
| 2 | BOEA/ACM 95/5 | yes | −36 | 2088 | 70 | 131 | interface | <10 |
| 3 | BOEA/ACM 97/3 | no | −48 | 2337 | 185 | 290 | interface | <10 |
| 4 | BOEA/ACM 99.9/0.1 | no | −57 | 2499 | 205 | 272 | interface | <10 |
| 5 | BOEA/ACM 99.9/0.1 | yes | −57 | 2272 | 86 | 83 | interface | <10 |
| 6 | HOEA/AA 95/5 | no | −47 | 1196 | 80 | 83 | interface | <10 |
| 7 | BOEA/NVP 85/15 | no | −36 | 2826 | 174 | 231 | interface | <10 |
| 8 | BOEA/NVP 85/15 | yes | −31 | 2570 | 71 | 128 | interface | <10 |
| 9 | BOEA/NVP 80/20 | no | −56 | 2852 | 140 | 185 | interface | <10 |
| 10 | BOEA/IOA/ACM 99.8/0.1/0.1 | no | −56 | 2651 | 211 | 280 | interface | <10 |
| 11 | BOEA/IOA/ACM 99.8/0.1/0.1 | yes | −56 | 2411 | 86 | 74 | interface | <10 |
| 12 | BOEA/IOA/ACM 95/4.9/0.1 | no | −48 | 2386 | 250 | 174 | interface | <10 |
| 13 | BOEA/IOA/ACM 60/37/3 | no | −43 | 1592 | 324 | 225 | interface | <10 |
| 14 | BOEA/IOA/ACM 55/42/3 | no | −42 | 1535 | 340 | 225 | interface | <10 |
| 15 | BOEA/IOA/ACM 51/46/3 | no | −41 | 1519 | 350 | 236 | interface | <10 |
| 16 | BOEA/IOA/ACM 60/37/3 | no | −43 | 1142 | 310 | 236 | interface | <10 |
| 17 | EOEA/IOA 80/20 | no | −43 | 2510 | 120 | 150 | interface | <10 |
| 18 | BOEA/MOEA/ACM 65/30/5 | yes | −32 | 2656 | 49 | 90 | interface | <10 |
| 19 | BOEA/MOEA/NVP 65/30/5 | yes | −40 | 3025 | 74 | 136 | interface | <10 |
| 20 | BOEA/EOA/NVP 70/10/15 | no | −41 | 3487 | 166 | 221 | interface | <10 |
| 21 | BOEA/EOA/ACM 85/10/5 | no | −40 | 2756 | 119 | 158 | interface | <10 |
| 22 | BOEA 100 | yes | −58 | 2665 | 90 | 75 | interface | <10 |
| 23 | 3-MBA/ACM 95/5 | no | −29 | 3155 | 45 | 80 | interface | <10 |

TABLE 2

| Comparative Examples | Composition/ Compounded Parts | Irradiation of γ-Rays | Tg (°C.) | Water Permeability (g/m · 24-hr.) | T0 (g/inch) | T48 (g/inch) | Failure Mode | LIFT (%) |
|---|---|---|---|---|---|---|---|---|
| 1 | AM90G/ACM 95 15 | no | −56 | 4948 | 74 | peeled | cohesion | — |
| 2 | AM90G/IOA/ACM 60/37/3 | no | −48 | 3892 | 137 | 43 | cohesion | >75 |
| 3 | BOEA/IOA/ACM 45/52/3 | no | −40 | 937 | 370 | 257 | interface | <10 |
| 4 | BOEA/MA 30/70 | no | −9 | 1668 | 21 | peeled | interface | — |
| 5 | BOEA/NVP 70/30 | no | −20 | 3416 | 60 | peeled | interface | — |
| 6 | MOEA/ACM 95/5 | no | −23 | 3005 | 19 | peeled | interface | — |

Notes in Tables 1 and 2
BOEA: butoxyethyl acrylate
EOBA: ethoxybutyl acrylate
HOEA: hexyloxyethyl acrylate
EOEA: ethoxyethyl acrylate
MOEA: methoxyethyl acrylate
AM90G: methoxypoly(ethylene glycol) acrylate having 9 repeating units of ethylene glycol (produced by Shin-Nakamura Kagaku K.K.)
IOA: isooctyl acrylate
ACM: acrylamide
NVP: N-vinyl-2 pyrrolidone
AA: acrylic acid
EOA: methoxypoly(ethylene glycol) acrylate having 16 repeating units of ethylene glycol (produced by 3M Company, St. Paul, Minnesota)
MA: methyl acrylate
3-MBA: 3-methoxybutyl acrylate

Effect of the Invention

According to the present invention, there is provided a pressure-sensitive adhesive for medical dressing material, having a high steam permeability (at least, 1100 g/($M^2$·24 Hr) at a temperature of 37° C. and an RH of 40%), and exhibiting such an appropriate initial adhesive strength as the dressing material coated with the pressure-sensitive adhesive is not easily peeled off and a wound is not inflicted on the skin when the dressing material is peeled from the skin. and also exhibiting durability of such an appropriate adhesive strength as well as an appropriate cohesive force.

We claim:

1. A medical pressure-sensitive adhesive, comprising a polymer containing a first unit derived from an alkoxyalkyl acrylate in an amount greater than 50 wt % in the polymer, and a second unit derived from a vinyl monomer in an amount ranging from 0.1 to 20 wt % in the polymer, wherein the Tg value of a homopolymer of the alkoxyalkyl acrylate is $-35°$ C. or less and the Tg value of a homopolymer of the vinyl monomer is at least 25° C. as measured by a dynamic viscoelasticity measuring device and wherein the pressure-sensitive adhesive has a steam permeability of at least 1100 g/$m^2$ for about 24 hours or more at 37° C. and an RH of about 40%, and wherein the adhesive strength of the adhesive is suitable for medical use.

2. A medical pressure-sensitive adhesive according to claim 1, wherein the alkoxyalkyl group of the alkoxyalkyl acrylate contains 4 to 8 carbon atoms.

3. A medical pressure-sensitive adhesive, according to claim 1, wherein the polymer additionally contains a unit derived from a second vinyl monomer, wherein the Tg value of a homopolymer of the second vinyl monomer is less than 25° C.

4. A medical pressure-sensitive adhesive in accordance with claim 1 wherein the Tg value of the polymer is $-10°$ C. or less.

5. A medical pressure sensitive adhesive according to claim 1 wherein the polymer is irradiated, so as to partially crosslink it.

6. A medical dressing material comprising a steam permeable substrate and a layer of steam permeable pressure-sensitive adhesive provided thereon, wherein the pressure-sensitive adhesive comprises a polymer containing a first unit derived from an alkoxyalkyl acrylate in an amount greater than 50 wt % in the polymer, and a second unit derived from a vinyl monomer in an amount ranging from 0.1 to 20 wt % in the polymer, wherein the Tg value of a homopolymer of the alkoxyalkyl acrylate is $-35°$ C. or less and the Tg value of a homopolymer of the vinyl monomer is at least 25° C. as measured by a dynamic viscoelasticity measuring device and wherein the pressure-sensitive adhesive has a steam permeability of at least 1100 g/$m^2$ for about 24 hours or more at 37° C. and an RH of about 40%, and wherein the adhesive strength of the adhesive is suitable for medical use.

7. The dressing material of claim 6, wherein the material is an adhesive tape.

* * * * *